(12) United States Patent
Hansen (10) Patent No.: US 11,666,675 B2
(45) Date of Patent: Jun. 6, 2023

(54) CHALLENGE DEVICE FOR USE WITH A MEASURING UNIT FOR TESTING STEAM STERILIZATION EFFICIENCY AND A METHOD OF MANUFACTURE OF A CHALLENGE DEVICE

(71) Applicant: ELLAB A/S, Hillerød (DK)

(72) Inventor: Rasmus Hansen, Hillerød (DK)

(73) Assignee: ELLAB A/S, Hillerød (DK)

( * ) Notice: Subject to any disclaimer, the term of this patent is extended or adjusted under 35 U.S.C. 154(b) by 819 days.

(21) Appl. No.: 16/583,943

(22) Filed: Sep. 26, 2019

(65) Prior Publication Data

US 2020/0101188 A1    Apr. 2, 2020

(30) Foreign Application Priority Data

Sep. 28, 2018   (EP) ..................................... 18197766

(51) Int. Cl.
*A61L 2/28* (2006.01)
*A61L 2/07* (2006.01)

(52) U.S. Cl.
CPC .................. *A61L 2/28* (2013.01); *A61L 2/07* (2013.01); *A61L 2202/123* (2013.01); *A61L 2202/14* (2013.01)

(58) Field of Classification Search
CPC ........ A61L 2/28; A61L 2/07; A61L 2202/123; A61L 2202/14; A61L 2202/24
See application file for complete search history.

(56) References Cited

U.S. PATENT DOCUMENTS

| 5,788,925 A | * | 8/1998 | Pai | ............................ A61L 2/28 422/26 |
| 2010/0036357 A1 | | 2/2010 | Bala | |
| 2018/0028704 A1 | * | 2/2018 | Stadler | .................... F28D 15/00 |

FOREIGN PATENT DOCUMENTS

| CN | 102688512 | 9/2012 |
| DE | 102007000632 | 5/2009 |
| EP | 1850102 A1 | 10/2007 |

OTHER PUBLICATIONS

EP Application No. 18197766, Search Report, dated Mar. 25, 2019, 2 pages.
EP Application No. 18197766, Extended European Search Report, dated Apr. 8, 2019, 1 page.

* cited by examiner

*Primary Examiner* — Patrick C Williams
(74) *Attorney, Agent, or Firm* — Avek IP, LLC (57) ABSTRACT

A challenge device for use with a measuring unit for testing steam sterilization efficiency, the challenge device comprising a measuring chamber, a first opening for insertion of a first temperature sensor of the measuring unit in the measuring chamber, and a second opening allowing air exchange between surroundings and the measuring chamber, where said air exchange is achieved by a hollow air flow passage. The measuring chamber is closed except for the first and second openings, and the air flow passage includes an outlet, which is located at a distance from the second opening in the direction of the length axis. The invention further relates to a method of manufacture of a challenge device.

9 Claims, 4 Drawing Sheets

CHALLENGE DEVICE FOR USE WITH A MEASURING UNIT FOR TESTING STEAM STERILIZATION EFFICIENCY AND A METHOD OF MANUFACTURE OF A CHALLENGE DEVICE

CROSS-REFERENCE TO RELATED APPLICATIONS

This application claims priority to EP Patent Application No. 18197766.1, filed Sep. 28, 2018, the disclosure of which is incorporated by reference in its entirety herein.

BACKGROUND

The invention relates to a challenge device for use with a measuring unit for testing steam sterilization efficiency. The measuring unit includes a base unit and at least two temperature sensors connected to at least one data receiver of the base unit, the challenge device having a proximal end adapted for being in contact with the measuring unit in a mounted state of the challenge device and a distal end adapted for facing away from the measuring unit in a mounted state. The challenge device includes a measuring chamber, a first opening for insertion of a first temperature sensor of the measuring unit in the measuring chamber, and a second opening allowing air exchange between surroundings and the measuring chamber. The first opening is adapted for insertion of a first temperature sensor in a direction parallel to a length axis of the challenge device, and the air exchange is achieved via a hollow air flow passage extending between the second opening and the measuring chamber. The invention further relates to a system including such a challenge device, to the use of such a system, and to a method of manufacturing a challenge device.

Such challenge devices and systems are used for testing the sterilization properties of, for example, autoclaves or sterilization chambers, such as in hospitals, dental clinics, or any other facility where steam sterilization is performed. Steam sterilization is a process widely used for sterilizing objects that are to be used where a high level of sterilization is required to avoid the presence of bacteria, viruses, etc. Some objects, such as surgical instruments, have shapes or surfaces that are difficult to access for the steam in a steam sterilization process. Particularly objects having edges, corners, long narrow channels or holes may be difficult to sterilize as the access for the sterilizing steam is difficult. It is therefore crucial that steam sterilization facilities and apparatuses are tested, to ensure that they are able to sterilize such objects to the required level of sterilization.

Such testing is typically done by inserting a test device with a so-called challenge device in the steam sterilization chamber, also known as an autoclave, and measuring if the steam manages to get through the challenge device. The test device may include a chemical indicator changing colour when exposed to heat and/or moisture or a biological indicator containing microorganisms which are killed when exposed to sufficient temperature and/or pressure. In recent years there has, however, been a trend towards using electronic temperature sensors and pressure sensors as these are generally more precise.

Challenge devices come in many forms, including stakes of paper and folded towels, but for use with electronic sensors the challenge devices typically include a labyrinth path which the steam must pass through in order to reach a measuring chamber, where a temperature sensor is located. Such devices are described in European Standard EN 867-5.

When using a labyrinth type challenge device, the first temperature sensor measures the temperature in the measuring chamber at the end of the labyrinth, while the second temperature sensor measures the temperature of the surroundings, e.g., the temperature in an autoclave. The challenge device creates a delay before steam reaches the first temperature sensor, and the labyrinth is designed so that sufficient sterilization is achieved when steam reaches the first temperature sensor. This may be measured by the first temperature sensor sensing the same temperature in the measuring chamber as the second temperature sensor measures in the surroundings, i.e., outside the challenge device, or by sufficiently low temperature gradient having been reached. By creating this delay, resistance, "challenge", or difficulty, the challenge device is thus used for testing the ability of a sterilization chamber or autoclave of reaching a required temperature and/or pressure during a required amount of time for sterilizing substantially all type of objects having surfaces that may be difficult to reach.

One example of a system comprising a challenge device for testing steam sterilization efficiency is disclosed in EP1850102A1. In this system a convex hollow member is arranged over a temperature sensor, which projects upwards from a measuring unit. A small opening in the hollow member allows steam from the sterilization chamber to flow into the measuring chamber underneath the hollow member and slowly displace the air trapped therein, eventually reaching the tip of the temperature sensor at the top of the hollow member.

This system provides fairly accurate measurements compared to many other systems but suffers from the disadvantage that it needs to cool down before it can be used for a new test, which may be problematic if needing to test several autoclaves at the same facility. Another disadvantage is that the hollow member may become wet on the inner side due to condensation and it is therefore necessary to open and dry the measuring chamber before the system can be used for a new test. Incomplete drying or incorrect reassembly of the system may result in imprecise measurements and consequently in wrong test results.

It is therefore one object of the invention to provide a challenge device and a system including a challenge device, which allows several tests to be performed with short intervals and which reduces the risk of errors due to incorrect assembly. A further object is to provide a challenge device which takes up as little space as possible.

SUMMARY OF THE INVENTION

According to a first aspect of the invention, these and further objects are achieved with a challenge device as mentioned above wherein the measuring chamber is closed except for the first and second openings, and where said air flow passage includes an outlet, which is located at a distance from the second opening in the direction of the length axis.

Having a closed measuring chamber already defined in the state of delivery of the challenge device, i.e. closed except for the first and second openings, instead of establishing the measuring chamber by connecting a hollow member to the measuring unit as in EP1850102A1, has several advantages.

Firstly, the fact that the challenge device and the measuring chamber are entirely independent of the measuring unit means that the challenge device can be easily be replaced.

This allows the same measuring unit to be used for several subsequent tests by simply replacing the challenge device with a new one before the next test. As a challenge device according to the invention will usually be considerably cheaper than the measuring unit, it will be feasible to have several challenge devices so that one can be allowed to cool off while using another or even to discard each challenge device after use.

Secondly, as the measuring chamber is already formed within the challenge device in the state of delivery, the challenge device may be mounted and replaced by an unskilled operator without risking that the measuring chamber becomes untight or otherwise affected by errors, which may lead to unreliable test results.

The fact that the air flow passage includes an outlet, which is located at a distance from the second opening in the direction of the length axis, means that the path travelled by the steam in the air flow passage is relatively long compared to challenge devices where the air flow passage extends straight through the chamber wall in a direction perpendicular to the wall. This means that any condensation forming during the steams first contact with challenge device will form within the air flow passage rather than in the measuring chamber. Furthermore, if the system is oriented with the length direction being substantially vertical and the challenge device upwards, as will usually be the case, any such condensation will be forced towards the first opening under the influence of gravity.

If the hollow air flow passage follows a non-linear path between the second opening and the outlet, it will be even longer as will be described in more detail below.

The challenge device according to the invention may be used with any type of measuring unit including a base unit and at least two temperature sensors connected to at least one data receiver of the base unit, and as several such measuring units are already available, it will not be described in detail here. It is, however, noted that the measuring unit may comprise further electronic components or hardware such as a processor, a pressure sensor, a data logger, a network interface controller, a network antenna, or any other suitable electronic component or hardware.

The challenge device may generally be circular in cross section when in the direction of the length axis. The cross section may alternatively also be oval, squared, triangular, or another suitable geometry.

The first opening may be located at the centre of the proximal end of the challenge device. This means that the first temperature sensor is isolated from the surroundings, which may contribute to reliable measurements performed by the first temperature sensor.

The first opening should preferably have a cross section matching the cross sectional shape of the first temperature sensor, although this is not required. The challenge device may comprise an elongated through hole between the first opening and the measuring chamber, such that the first temperature sensor may be further isolated from the surroundings and may be guided through the through hole into the chamber.

In some embodiments the first opening corresponds substantially in size to the outer dimensions of the first temperature sensor, the first opening preferably being slightly bigger than the first temperature sensor to avoid difficulties of insertion and damage of the first temperature sensor.

The first opening may further comprise, for example, a gasket seal to improve the sealing of the measuring chamber. By having a first opening which corresponds substantially in size to the outer dimensions of the first temperature sensor, the first temperature sensor may be guided into the measuring chamber.

In some embodiments, at least a section of the hollow air flow passage is spiral-shaped and extending in an outer wall of the challenge device between the second opening and the outlet.

The spiral-shaped hollow air flow passage may extend in the outer wall of the challenge device in a twisted or winded manner around the challenge device along the length axis. By having a spiral-shaped hollow air flow passage the length of the hollow air flow passage may be increased while keeping a compact challenge device and the challenge or resistance to the steam penetration may thus be increased.

The optimal dimension of the hollow air flow passage depends on several factors, such as the material(s) used for the challenge device and size and shape of the measuring chamber.

In some embodiments the challenge device further comprises an inner wall extending inside the challenge device in parallel with the outer wall, where the inner wall delimits the measuring chamber and where a space between the outer wall and the inner wall forms a section of the hollow air flow passage.

By providing a section of the hollow air flow passage in a space between the outer wall and the inner wall, the hollow air flow passage may be extended and provide further challenge to the system. By for example combining a section of the hollow air flow passage in the space between the outer wall and the inner wall and a spiral-shaped hollow air flow passage in the outer wall, the challenge or resistance of the challenge device may be increased.

The measuring chamber may have a smaller volume when a section of the hollow air flow passage is a space between the outer wall and an inner wall. The optimal dimensions of the measuring chamber depend on several factors, such as the material(s) used for the challenge device and the geometry of the hollow air flow passage.

The thickness of one or more walls of the challenge device may be varied in order to vary the insulation properties of the challenge device.

In one embodiment the challenge device has an outer diameter of less than 100 mm, preferably less than 80 mm, more preferably less than 50 mm, and most preferably less than 30 mm.

The distance between an outermost surface of the proximal end and outermost surface of the distal end of the challenge device define a length of the challenge device. In one embodiment this length of the challenge device is less than 100 mm, less than 80 mm, less than 50 mm, or even less than 30 mm.

In some embodiments, the challenge device further comprises an insulating cover that may be arranged on the challenge device for improving the insulation of the measuring chamber. The insulating cover may be of silicone or other types of flexible insulating materials. Such a cover may also be used for achieving desired surface properties of the challenge device, such as friction, in order to facilitate handling of the challenge device and/or the system when the challenge device is mounted on a measuring unit.

What is understood by the second opening allowing air exchange between surroundings and the measuring chamber is that the second opening allows air exchange between surroundings and the measuring chamber at all time, even when the challenge device is in the mounted state, i.e., connected to the measuring unit.

In some embodiments the second opening is positioned so that it will be facing the base unit in the mounted state of the challenge device. This may contribute to avoiding that the second opening becomes blocked, covered, or obstructed e.g. when the challenge device is positioned laying down with the second opening oriented downwards. This may thereby reduce the risk of erroneous measurements, and may facilitate the handling and operation of the challenge device for a user operating a sterilization test.

The challenge device may be made in one piece e.g. by 3D printing, moulding or the like, but in some embodiments the challenge device comprises a first part forming the distal end of the challenge device and a second part forming the proximal end of the challenge device, the first and second parts being irreversibly interconnected in the state of delivery of the challenge device and together delimiting the measuring chamber.

The second part may be inserted in the first part and irreversibly interconnected therein in the delivery state. The opposite where the first part is inserted into the second is also possible and so is an embodiment, where the two parts do not overlap but simply abut on each other.

The first and second part may be form-fitted to each other, whereby the connection of the second part to the first part is achieved by press-fitting, although moulding, gluing, etc. is also possible.

The first and second parts may generally be shaped as hollow cylinders that are open on one end, where the diameter of the first part may be bigger than the diameter of the second part or alternatively the diameter of the second part may be bigger than the diameter of the first part. The second part may thereby be inserted in the first part, and the hollow space of the second part being closed on one end by the first part, thereby forming the measuring chamber. A similar effect may be achieved by the first part being embodied as a cap, a plug or the like.

The second part may have a length such that when inserted in the first part, the second part projects from the first part or vice versa.

The first opening may be provided in the second part, and the second opening may be provided in the first and/or the second part.

In some embodiments the first part of the challenge device and the second part of the challenge device each comprise an outer wall section, these outer wall sections together forming the outer wall of the challenge device, and where a spiral-shaped groove in a surface of one of these outer wall sections facing the other outer wall section forms a spiral-shaped section of the hollow air flow passage.

A spiral-shaped groove may be in a surface of the outer wall section of the second part, said surface of the outer wall section of the second part facing the outer wall section of the first part. Alternatively, a spiral-shaped groove may be in a surface of the outer wall section of the first part, said surface of the outer wall section of the first part facing the outer wall section of the second part. By having the spiral-shaped groove formed in such a manner the challenge device may, for example, be made compact. Grooves in both the first and second parts matching each other may also together form the hollow air flow passage, but this will require high precision when interconnecting the two parts.

The first part and the second part may be irreversibly interconnected to each other. By having the first part and the second part irreversibly interconnected to each other, the challenge device cannot be taken apart, and the measuring chamber can therefore not be compromised by improper handling or manipulation by a user. This may further lower the risk of error due to parts of the challenge device not being correctly connected, disconnected, attached, or re-attached.

In some embodiments the challenge device comprises at least one connector for connecting the challenge device to the base unit, such as a thread and/or a sealing gasket, is provided at the proximal end.

A sealing gasket may for example be provided on an exposed surface of the challenge device extending perpendicular to the length axis, so that it may be pressed against a surface of the base unit facing the challenge device in the mounted state.

A challenge device may include a groove for accommodating a sealing gasket that is provided in an exposed surface of the challenge device and extends substantially in parallel with the length axis. The exposed surface may possibly also be provided with a thread. In other words, the connector may be an outer threaded portion corresponding to an inner threaded portion of the base unit, or the connector may be an inner threaded portion corresponding to an outer threaded portion of the base unit, whereby the challenge device may be detachably attached to the base unit by being screwed on and off.

The connector may alternatively be magnetic such that the challenge device may be attached and detached in a faster manner, or the connector may be a friction fitting, e.g. if the challenge device and the measuring unit are form fitted to each other, the challenge device may be press-fitted into the measuring unit, or the measuring unit may be press-fitted into the challenge device. A snap-lock connector adapted for engagement with a projection or depression on/in the base unit is also envisaged.

It is to be understood that the different means for connecting the challenge device to the base unit may also be combined.

When the challenge device comprises a first and a second part, an outer surface of the second part projecting from the first part may comprise the connector, e.g. as an outer threaded portion corresponding to an inner threaded portion of the base unit, whereby the challenge device may be detachably attached to the base unit.

A sealing between the challenge device proximal end and the measuring unit may be facilitated by compressing a sealing gasket between the challenge device and the measuring unit. For this purpose, the challenge device may comprise a circular recess arranged at the proximal end to receive a sealing gasket. A gasket may, for example, be pressed against the base unit when mounting the challenge device on the measuring unit by screwing a challenge device with a threaded connector onto the base unit.

The measuring unit may comprise a substantially planar contact surface surrounding the first temperature sensor. When mounted on the measuring unit, the gasket may be pressed against this contact surface and the proximal end may thereby abut on the contact surface. This embodiment, however, prevents unintentional movement of the challenge device away from the base unit along the length axis since it might cause an interruption of the sealing provided by the sealing gasket.

It is, however, also possible to provide a sealing gasket on the base unit and leaving the challenge device with a substantially plane contact surface surrounding the first opening, or to provide both with sealing gaskets.

Many different materials can be used for the challenge device including polymers, metals, ceramics, and composites. The choice of material depends on several factors, such as resistances to heat and moisture, but thermal capacity and thermal conductivity are also very important as they will influence on the temperature profile measured by the first temperature sensor. Materials having a relatively low thermal conductivity may be preferred to improve the insulation properties of the challenge device. In some embodiments the challenge device or part of the challenge device is made from polyether-ether-ketone (PEEK), Polytetrafluoroethylene (PTFE) and/or Polyphenylene sulfide (PPS).

A challenge device may be composed of more than one material in order to achieved desired thermal properties. In one embodiment, the challenge device comprises a sleeve arranged in a space delimited by an outer wall, where the measuring chamber is a least partially delimited by the sleeve. By for example making this sleeve from surgical steel, both the overall thermal capacity of the challenge device and the overall thermal conductivity becomes higher than if using a challenge device, where the same volume was occupied by PEEK. By choosing a sleeve made from an appropriate material, it will thus be possible to adapt the thermal properties of the challenge device to specific requirements. Using different materials at different sections of the hollow air flow passage may also contribute to optimizing measurement precision and/or preventing unintentional condensation.

In one embodiment, the sleeve is made from surgical steel while the rest of the challenge device (excluding possible gaskets) is made from PEEK, and the sleeve constitutes 15-40%, preferably 20-35%, still more preferred about 25% of the total solid volume of the challenge device. By total solid volume is meant the volume of the challenge device occupied by solid materials, in other words retracting the volume occupied by hollows within the challenge device from the total volume of the challenge device.

It is also possible to make the first and second parts mentioned above from different materials in order to achieve similar effects.

A second aspect of the invention relates to a system for testing steam sterilization efficiency, comprising a challenge device according to the first aspect of the invention, the challenge device being mounted on a measuring unit including a base unit and at least two temperature sensors connected to at least one data receiver of the base unit, wherein the challenge device is detachably attached to the measuring unit.

Having a system for testing steam sterilization efficiency having a challenge device that is detachably attached to the measuring unit, may, for example, allow the challenge device to be exchanged between testing, e.g. if the temperature of the challenge device is too high, which may give erroneous measurements, or if the challenge device is too humid. This may further make it possible to adapt e.g. the system to the type of testing or the sterilization chamber or autoclave to be tested by choosing a suitable challenge device. The challenge device may thereby be exchanged by another challenge device, while keeping the same measuring unit, for the next testing. A further advantage may be to reduce the time interval between tests and measurements, if e.g. several challenge devices are available.

A third aspect of the invention relates to the use of a system according to the second aspect of the invention for testing steam sterilization efficiency, wherein the challenge device is exchanged for every new test.

By exchanging the challenge device for every new test, the challenge device may be provided as disposable one-use items. Some applications may require that the challenge device is exchanged for every new test for example in order to achieve particularly precise measurements.

A further embodiment of the invention relates to a method of manufacture of a challenge device according to a first aspect of the invention, comprising the steps of: forming the hollow air flow passage in the second part of the challenge device; and establishing irreversibly interconnection of the first part and the second part. In some embodiments, the method further includes the steps of: cutting the second part along an outer wall section surface adapted to face an outer wall section of the first part, from one end of the outer wall section of the second part to the opposite end of the outer wall section of the second part in a rotational movement along the length axis, whereby a spiral-shaped groove is formed; and press fitting the second part into the first part, whereby a spiral-shaped hollow air flow passage is formed between the first and the second part.

BRIEF DESCRIPTION OF THE DRAWINGS

In the following, the invention will be described in more detail with reference to the drawings, where.

DETAILED DESCRIPTION

Figure 1:
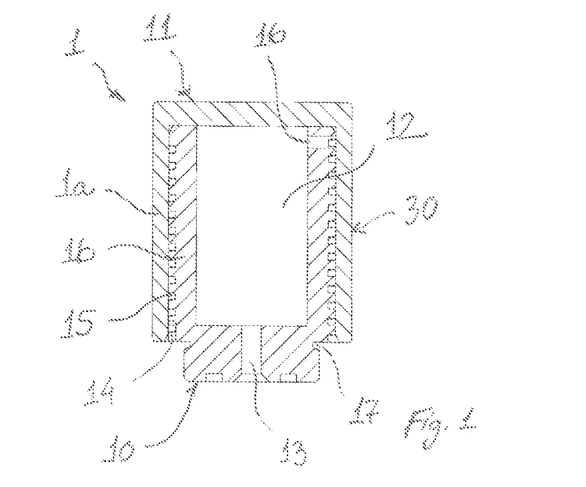
FIG. 1 is a cross-sectional view of a challenge device.
Figure 2:
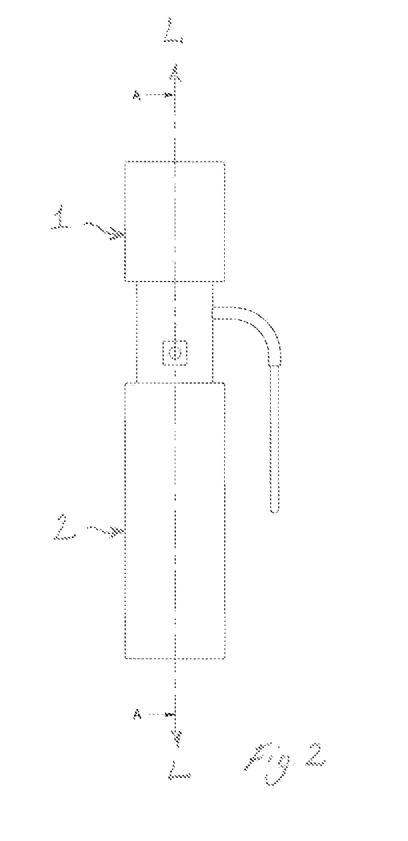
FIG. 2 is a side view of a challenge device mounted on a measuring unit.

A challenge device 1 for use in testing steam sterilization efficiency is shown in cross-section in FIG. 1 and FIG. 2 shows a side view of a system where the challenge device is mounted on a measuring unit 2. A proximal end 10 of the challenge device is in contact with the measuring unit and a distal end 11 faces away from the measuring unit 2.

Figure 3:
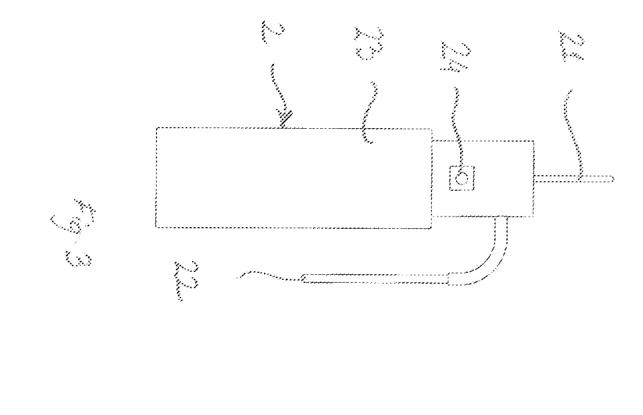
FIG. 3 is a side view of a measuring unit.

The measuring unit 2, which is shown from the side without the challenge device in FIG. 3, includes a first temperature sensor 21 and a second temperature sensor 22 both projecting from a base unit 23 and a pressure sensor 24 embedded in the base unit 23. The base unit 23 includes at least one data receiver (not shown) to which the two temperature sensors, and possibly also the pressure sensor 24, are connected. Further component (not shown) adapted for allowing collection, storage, and transmittal of data or for performing other measurements may be included in the base unit 23. Other embodiments of the measuring unit 2 are possible, but will not be described in detail here.

Figure 4:
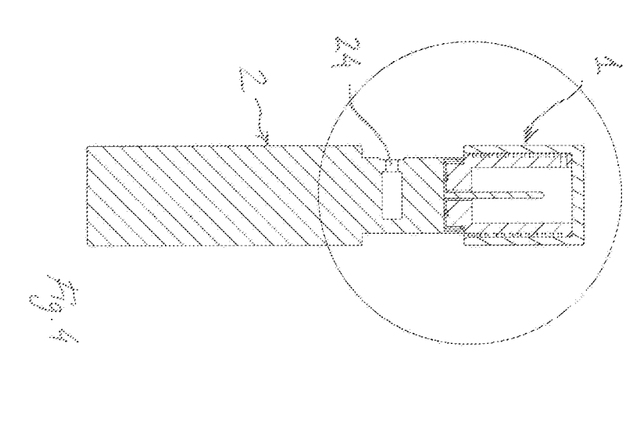
FIG. 4 is a cross-sectional view of the challenge device in FIG. 1 mounted on a measuring unit as in FIG. 2.
Figure 5:
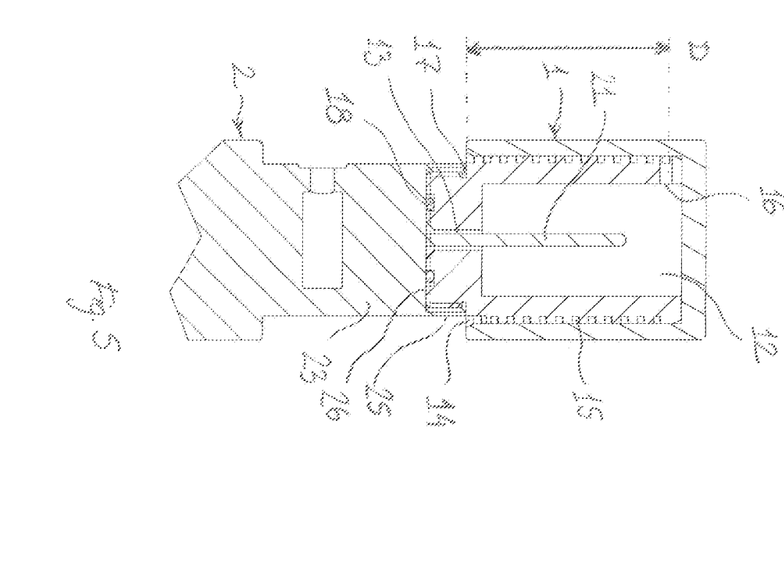
FIG. 5 is an enlargement of the uppermost part of FIG. 4.

The challenge device 1 comprises a measuring chamber 12 and a first opening 13 for insertion of the first temperature sensor 21 of the measuring unit 2 in the measuring chamber as is shown in FIGS. 4 and 5. The first opening 13 is provided at the proximal end 10 of the challenge so that first temperature sensor 21 extends in a direction parallel to a length axis L of the challenge device in the mounted state of the challenge device.

A second opening 14 serves as an inlet to a hollow air flow passage 15 extending between the second opening 14 and the measuring chamber 12 thus allowing air exchange between surroundings and the measuring chamber 12. As is seen from FIG. 1 the measuring chamber 12 is closed in the state of delivery of the challenge device 1 except for the first and second openings 13, 14.

The hollow air flow passage is here spiral-shaped and ending at an outlet 16 at the distal end 11 of the challenge device, i.e. at a distance D from the second opening 14 measured in parallel with the length direction L as indicated in FIG. 5.

In embodiments, the challenge device 1 is made from two parts 1a, 1b, which are irreversibly interconnected to each other, the first part 1a forming the distal end 11 of the challenge device and the second part 1b forming the proximal end. The first and second parts 1a, 1b together delimit the measuring chamber 12. Each part 1a, 1b comprises an outer wall section and these outer wall sections together form the outer wall 30 of the challenge device.

In embodiments, the two parts 1a and 1b are interconnected by press fitting, but it is within the scope of the invention to establish or reinforce the interconnection in another way, including gluing, welding, and snap-locking.

Figure 6:
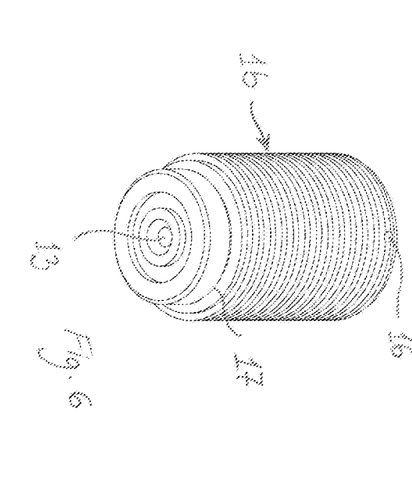
FIG. 6 is a perspective view of a second part of the challenge device in FIG. 1.

The spiral-shaped hollow air flow passage 15 may be formed as a groove in the outer surface of the outer wall of the second part 1b facing the inner surface of the outer wall of the first part 1a. This groove is best seen in FIG. 6, which shows the second part 1b in a perspective view.

The fact that the first and second parts 1a, 1b are irreversibly connected in the stat of delivery entails that the measuring chamber 12 is well-defined and that the risk of air or steam penetrating between the two parts is low. To further reduce the risk of unintended air exchange between the surroundings and the measuring chamber 12, the first opening 13 corresponds substantially in size to the outer dimensions of the first temperature sensor 21, leaving just enough space to allow a safe insertion of the first temperature sensor 21 in the measuring chamber 12.

A still further feature, which reduces the risk of unintended air exchange between the surroundings and the measuring chamber 12, is the connectors 17, 18 provided at the proximal end of the challenge device for connecting the challenge device to the base unit 23. In this embodiment a groove 17 comes into a snap-locking engagement with a flange 25 on the base unit and a sealing gasket 18 is compressed between the proximal end 10 of the challenge device and a contact surface 26 of the base unit 23. It is, however, also possible to interconnect the challenge device 1 to the measuring unit 2 in another way such as for example by providing the challenge device and the flange 25 of the base unit 23 with matching threads.

As is seen in FIG. 5 the second opening 14 is here provided in a surface of the challenge device 1 facing the base unit 23, but which is not covered by the base unit 23 in the mounted state of the challenge device 1. This has the advantage that the second opening 14 will not be blocked if the system with the challenge device 1 mounted on the measuring unit 2 is lying down or is placed close to another object, hence reducing the risk of measurement errors.

Figure 7:
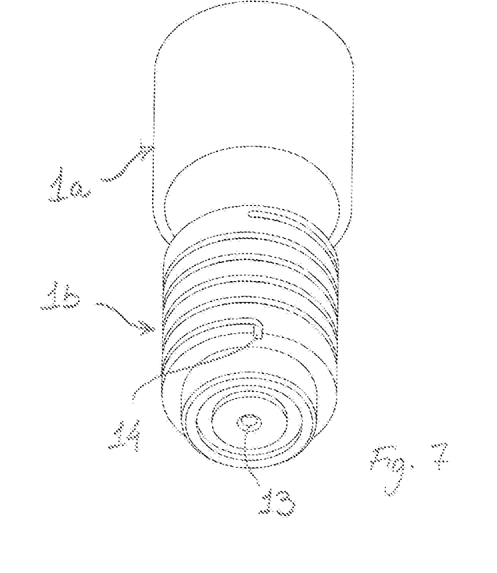
FIG. 7 is a perspective exploded view of a further embodiment of a challenge device.
Figure 8:
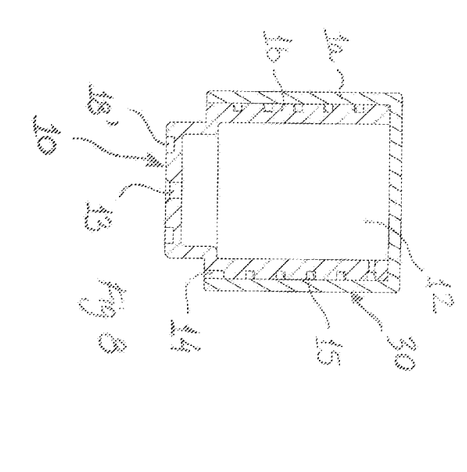
FIG. 8 is a cross-sectional view of the challenge device in FIG. 7.

A simpler embodiment of a challenge device is shown in FIGS. 7 and 8. In these figures as well as in the rest of the drawings and in the description relating thereto the same reference numbers as in FIGS. 1-6 will be used for features having substantially the same function.

In the embodiment in FIGS. 7-8 the hollow air flow passage 15 is shorter and the measuring chamber 12 larger and with a different geometry than in the embodiment in FIGS. 1-6. Furthermore, the challenge device 1 does not have a connector groove for interconnection to the base unit, meaning that this challenge device 1 is kept in place on the measuring unit 2 only by gravity and/or friction between the proximal end 10, possibly a gasket arranged in the groove 18', and a flange on the base unit corresponding to the flange 25 in FIG. 5. Friction between the first temperature sensor 21 and the first opening 13 may, however, also contribute to keeping the challenge device in place on the measuring unit 2.

The second part 1b of the challenge device in FIGS. 7-8 is adapted for being made by milling whereas the second part 1b of the challenge device in FIGS. 1-6 is adapted for being made by cutting.

Figure 9:
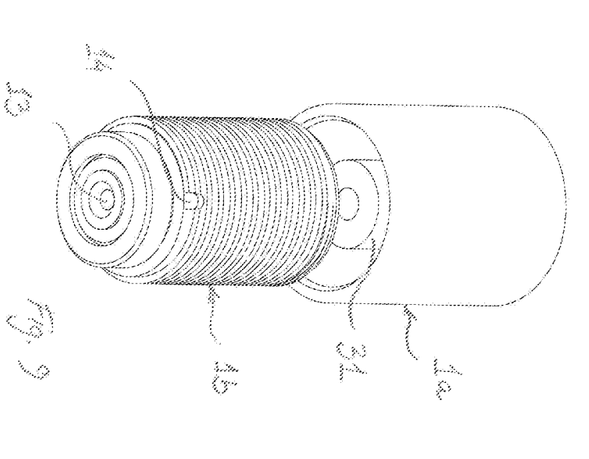
FIG. 9 is a perspective exploded view of a still further embodiment of a challenge device.
Figure 10:
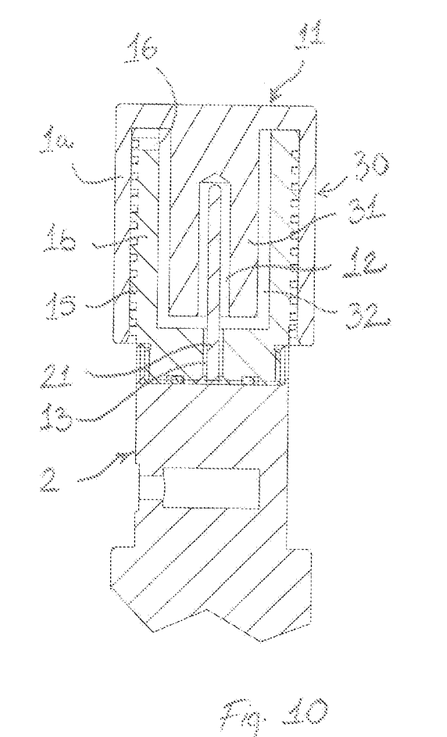
FIG. 10 is a cross-sectional view of the challenge device in FIG. 9 mounted on a measuring unit as in FIG. 2.

A still further embodiment is shown in FIGS. 9-10. In this embodiment the first part 1a further comprises an inner wall 31 extending from the distal end 11 inside the challenge device in parallel with the outer wall 30. The inner wall 31 delimits the measuring chamber 12, where the first temperature sensor 21 is located in the mounted state of the challenge device, and a space 32 is present between the outer wall 30 and the inner wall 31. This space 32 forms a second section of the hollow air flow passage extending between the outlet 16 from the first spiral-shaped section 15 of the hollow air flow passage and the measuring chamber 12. When having passed through the spiral-shaped first section 15 of the hollow air flow passage the steam will have to first descend between the outer and inner walls 30, 31 and then rise, climb, or ascend into the measuring chamber 12 to reach the tip of the first temperature sensor 21. This embodiment thus provides a challenge device where air or steam will have to travel further to reach the tip of the first temperature sensor 21 than in the embodiment in FIGS. 1-6 and where the larger amount of material in the first part 1a will contribute to keeping the temperature in the measuring chamber down by adding thermal capacity.

Another embodiment with the potential for increased thermal capacity compared to the embodiments in FIGS. 1-8 is shown in FIGS. 11-14. Here a sleeve 19 made from a different material than the first and second parts 1a, 1b has been inserted into the second part 1b. The sleeve has an outer diameter corresponding to the inner diameter of the second part 1b, so that it is prevented from moving sideways during use. This provides a tight contact between the second part and the sleeve and prevents the sleeve from damaging the first temperature sensor 21.

The sleeve 19 may be made from any material, which tolerates the humidity and temperatures occurring during use of the challenge device, and which provides the challenge device with a desired thermal capacity. This means that challenge devices with different thermal capacities can be provided by using different sleeves while the same first and second parts 1a, 1b remain the same. In this way it is possible to provide challenge devices where the time until a particular temperature is reached within the measuring chamber is different.

It is noted that even though the sleeve 19 is here shown in a challenge device where a spiral-shaped air flow passage 15 is formed between the inner side of a first part 1a and a groove in an outer side of a second part 1b, the sleeve may also be employed in other embodiments. One example is a challenge device where the air flow passage is not spiral-shaped. It is even possible for the sleeve to delimit at least a section of the air flow passage.

Figure 11:
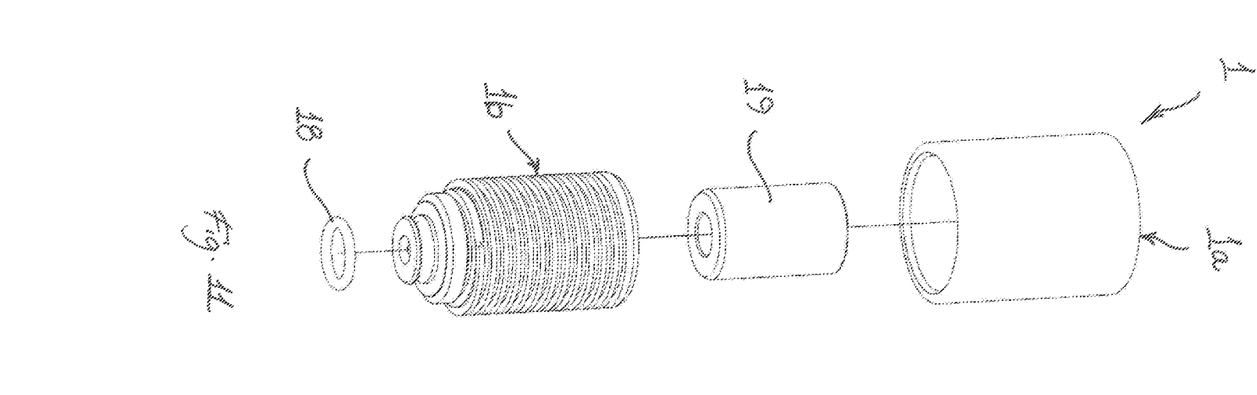
FIG. 11 is a perspective exploded view of a still further embodiment of a challenge device.
Figure 12:
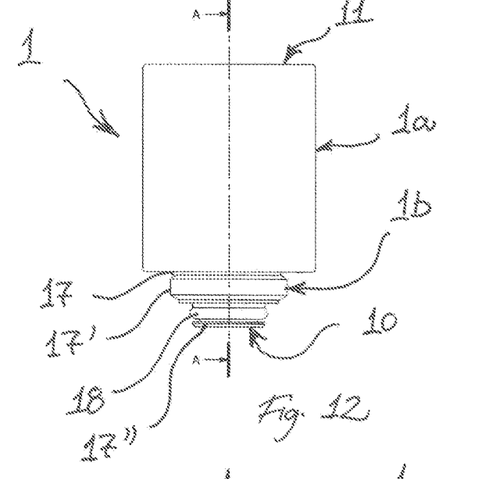
FIG. 12 is a side view of the challenge device in FIG. 11.
Figure 13:
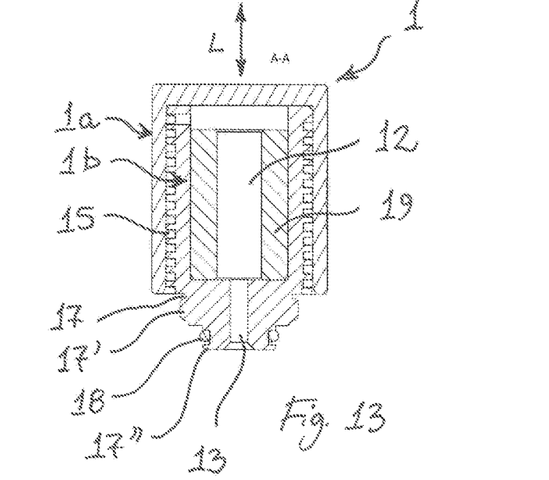
FIG. 13 is a cross-sectional view of the challenge device in FIGS. 11 and 12.
Figure 14:
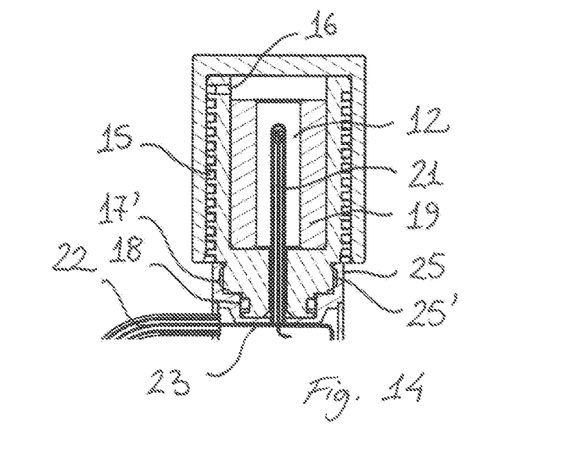
FIG. 14 is a cross-sectional view corresponding to FIG. 13 but showing the challenge device mounted on a measuring device.

The challenge device in FIGS. 11-13 further differs from those in FIGS. 1-10 in that the sealing gasket 18 is provided in a groove in an exposed surface of the challenge device extending substantially in parallel with the length axis L. As may been seen in FIG. 14 this means that the sealing gasket 18 comes into contact with an inner surface of base unit 23 extending substantially in parallel with the length axis L instead of a surface extending perpendicular to the length axis as in FIGS. 4, 5 and 10. This has the advantage that even if the challenge device moves slightly away from the base unit along the length axis the sealing provided by the sealing gasket 18 will not be interrupted.

A thread (not shown) adapted for engaging with a corresponding thread 25' in the flange 25 on the base unit may be provided on the exposed surface 17' also extending substantially in parallel with the length axis L in the mounted state, so that the challenge device may be screwed onto the base unit 23 of the measuring device. Such threads may also be provided on the challenge devices in FIGS. 1-10.

Many different arrangements of the described invention are possible without departing from the spirit and scope of the invention. Embodiments of the invention are described herein with the intent to be illustrative rather than restrictive. Alternative embodiments will become apparent to those skilled in the art that do not depart from its scope. A skilled artisan may develop alternative means of implementing the disclosed improvements without departing from the scope of the invention.

Further, it will be understood that certain features and subcombinations are of utility and may be employed without reference to other features and subcombinations and are contemplated within the scope of the claims. Not all steps listed in the various figures and description need to be carried out in the specific order described. The description should not be restricted to the described embodiments.

What is claimed is:

1. A system for testing steam sterilization efficiency, comprising:
 a challenge device detachably attached to a measuring unit, wherein:
 the measuring unit comprises a base unit and at least two temperature sensors connected to at least one data receiver of the base unit; and
 the challenge device has a proximal end in contact with the measuring unit where at least one connector for connecting the challenge device to the base unit is provided at the proximal end, and a distal end facing away from the measuring unit, and comprises:
 a measuring chamber;
 a first opening for insertion of a first temperature sensor of the measuring unit in the measuring chamber; and
 a second opening allowing air exchange between surroundings and the measuring chamber
 wherein:
 the first opening is adapted for insertion of the first temperature sensor in a direction parallel to a length axis of the challenge device;
 the air exchange is achieved via a hollow air flow passage extending between the second opening and the measuring chamber;
 the measuring chamber is closed except for the first and second openings;
 the air flow passage includes an outlet located at a distance from the second opening in the direction of the length axis; and
 the second opening is positioned so that it faces an exterior of the base unit.

2. The system according to claim 1, wherein at least a section of the hollow air flow passage is spiral-shaped and extending in an outer wall of the challenge device between the second opening and the outlet.

3. The system according to claim 1, wherein the challenge device comprises a first part forming the distal end of the challenge device and a second part forming the proximal end of the challenge device, the first and second parts being irreversibly interconnected and together delimiting the measuring chamber.

4. The system according to claim 3, wherein the first part of the challenge device and the second part of the challenge device each comprises an outer wall section, these outer wall sections together forming the outer wall of the challenge device, and wherein a spiral-shaped groove in a surface of one of these outer wall sections facing the other outer wall section forms the spiral-shaped section of the hollow air flow passage.

5. The system according to claim 1, wherein a groove for accommodating a sealing gasket is provided in an exposed surface of the challenge device, the exposed surface extending substantially in parallel with the length axis, the exposed surface optionally being provided with a thread.

6. The system according to claim 1, wherein said challenge device or part of the challenge device is made from polyether-ether-ketone (PEEK) and/or polytetrafluoroethylene (PTFE).

7. The system according to claim 1, wherein the challenge device further comprises a sleeve arranged in a space delimited by an outer wall, wherein the measuring chamber is a least partially delimited by the sleeve.

8. The system according to claim 1, wherein the first opening corresponds in size to the outer dimensions of the first temperature sensor.

9. The system of claim 1, wherein the challenge device is configured to be exchanged for every new test.

* * * * *